United States Patent [19]
Wagner et al.

[11] Patent Number: 6,156,921
[45] Date of Patent: *Dec. 5, 2000

[54] METHOD AND APPARATUS FOR DIRECT OXYGEN INJECTION WITH A REACTANT STREAM INTO A FLUIDIZED BED REACTOR

[75] Inventors: Matthew Lincoln Wagner, White Plains; Thomas John Bergman, Jr., Clarence Center, both of N.Y.

[73] Assignee: Praxair Technology, Inc., Danbury, Conn.

[ * ] Notice: This patent is subject to a terminal disclaimer.

[21] Appl. No.: 09/037,980

[22] Filed: Mar. 9, 1998

Related U.S. Application Data

[62] Division of application No. 08/519,011, Aug. 24, 1995, Pat. No. 5,801,265.

[51] Int. Cl.[7] .................... C07C 253/24; C07C 253/26; C07C 253/18
[52] U.S. Cl. .............................................. 558/320
[58] Field of Search ............................. 558/320

[56] References Cited

U.S. PATENT DOCUMENTS

| | | | |
|---|---|---|---|
| 3,661,165 | 5/1972 | Rainbird et al. | 137/100 |
| 4,609,502 | 9/1986 | Khoobiar et al. | 558/320 |
| 4,754,049 | 6/1988 | Khoobiar et al. | 558/320 |
| 4,849,537 | 7/1989 | Ramachandran et al. | 558/319 |
| 4,849,538 | 7/1989 | Ramachandran et al. | 558/319 |
| 4,868,330 | 9/1989 | Ramachandran et al. | 558/320 |
| 4,870,201 | 9/1989 | Ramachandran et al. | 558/319 |
| 5,015,756 | 5/1991 | Ramachandran et al. | 558/320 |
| 5,356,213 | 10/1994 | Arpentinier | 366/178 |
| 5,801,265 | 9/1998 | Wagner et al. | 568/320 |

FOREIGN PATENT DOCUMENTS

| | | |
|---|---|---|
| 61-13700 | 4/1986 | Japan . |
| 1569476 | 6/1980 | United Kingdom . |

*Primary Examiner*—Floyd D. Higel
*Attorney, Agent, or Firm*—Bernard Lau

[57] ABSTRACT

A system provides an oxygen-bearing gas and a gaseous reactant stream to a fluidized bed reactor. A sparger causes an entraining of the oxygen bearing gas into the reactant gas stream. A feed line couples the sparger to the reactor's fluidized bed and introduces the reactant gas stream and entrained oxygen-bearing gas directly into contact with the fluidized bed. A controller controls both the amount of oxygen-bearing gas and the gaseous reactant so that, at the point of feed injection, the fluidized bed catalyst does not experience an oxygen deficiency. To assure safety, the reactant content of the combined feed and oxygen stream is maintained above an upper flammability limit, preferably with a safety margin of at least 25%. In one embodiment, the system enables the production of acrylonitriles from a feed stream comprising ammonia, propylene and oxygen.

10 Claims, 2 Drawing Sheets

METHOD AND APPARATUS FOR DIRECT OXYGEN INJECTION WITH A REACTANT STREAM INTO A FLUIDIZED BED REACTOR

This Application is a Division of Ser. No. 08/519,011 filed Aug. 24, 1995, U.S. Pat. No. 5,801,265.

FIELD OF THE INVENTION

This invention relates to a method and apparatus for entraining an oxygen-bearing gas in a reactant stream which is fed to a fluidized bed reactor and, more particularly, for injection of oxygen into a reactant feed stream to a fluidized bed reactor that is employed in an acrylonitrile synthesis process.

BACKGROUND OF THE INVENTION

The production of nitrites involves ammoxidation of an appropriate alkene in the presence of a suitable catalyst. Acrylonitrile production employs feeds of propylene and ammonia into an ammoxidation reactor where, in the presence of air/oxygen and a suitable catalyst, acrylonitrile is produced with lesser amounts of other nitrogen-containing compounds and carbon oxides. The reactor is often a fluidized bed reactor which includes a separate air injection conduit for introduction of either air or enriched air (with added oxygen) into the fluidized bed. Effluent from the ammoxidation reaction is quenched with water, as desired products are recovered in the liquid phase.

To provide oxygen for the conversion of the mixture of propylene and ammonia to acrylonitrile, the prior art has suggested the addition of oxygen or oxygen-containing gas directly to the feed flow or as a separate feed to the reactor. Such teachings can be found in U.S. Pat. No. 4,609,502 to Khoobiar et al. and U.S. Pat. No. 4,868,330 of Ramachandran et al. Neither of the aforesaid patents provides any teaching that an oxygen deficiency can occur in a fluidized bed reactor at the point of reactant feed introduction. Ramachandran et al. teach that when a pure oxygen feed is present in the ammoxidation reactor, that a gaseous flame suppressor mixture be utilized, e.g., carbon dioxide in an amount of about 25–70% by volume. As a result, Ramachandran et al. provides further apparatus downstream from the ammoxidation reactor to recover and recycle the carbon dioxide.

Other references which teach further details regarding acrylonitrile production are: U.S. Pat. No. 4,754,049 to Khoobiar et al.; and U.S. Pat. Nos. 4,849,537, 4,849,538, 4,870,201 and 5,015,756, all to Ramachandran et al. While, as above indicated, the prior art teaches the addition of oxygen or oxygen-bearing gases into a feed stream to an ammoxidation reactor, none of the cited patents provide details as to equipment for such gaseous addition/mixing.

U.S. Pat. No. 3,661,165 to Rainbird et al. discloses a sparger valve for the mixing of oxygen with gaseous hydrocarbons in a process stream. The Rainbird et al. sparger valve includes a number of jets facing downstream within the hydrocarbon gas flow. The jets introduce oxygen at a jet velocity that is substantially higher than the velocity of the hydrocarbon gas. Variations in oxygen mass flow are achieved by varying the area of the jet orifices, while maintaining a predetermined pressure drop across the orifices.

U.S. Pat. No. 5,356,213 to Arpentinier describes a further sparger design which is positioned coaxially with respect the axis of a channel containing a feed stream. Radial vanes are employed in the sparger to enable injection of gas in a substantially radial direction towards the outside of the feed flow so as to enable a mixing of the injected gas with the feed flow gas.

The above noted prior art includes no teaching of fluidized bed reactor performance penalties which occur as a result of oxygen deficiencies at points of feed stream introduction. Further, the prior art, while including teachings regarding the introduction of oxygen-bearing gases at various points in a process, includes no teachings of how such an introduction can be accomplished in a manner to assure process safety.

Accordingly, it is an object of this invention to provide an improved system for enabling an oxygen bearing gas to be combined with a gaseous reactant feed flow to a fluidized bed reactor.

It is another object of this invention to provide an improved system and method for combining an oxygen-bearing gas and gaseous reactants in a manner to avoid explosions, deflagration or other anomalous effects in the process.

It is yet another object of this invention to provide an improved method and system for addition of oxygen to ammonia and propylene gaseous reactants in a fluidized bed reactor wherein oxygen deficiencies at feed flow entries are avoided.

SUMMARY OF THE INVENTION

A system provides an oxygen-bearing gas and a gaseous reactant stream to a fluidized bed reactor. A sparger causes an entraining of the oxygen-bearing gas into the reactant gas stream. A feed line couples the sparger to the reactor's fluidized bed and introduces the reactant gas stream and entrained oxygen-bearing gas directly into contact with the fluidized bed. A controller controls both the amount of oxygen-bearing gas and the gaseous reactant so that, at the point of feed injection, the fluidized bed catalyst does not experience an oxygen deficiency. To assure safety, the reactant content of the combined feed and oxygen stream is maintained above an upper flammability limit, preferably with a safety margin of at least 25%. In one embodiment, the system enables the production of acrylonitriles from a feed stream comprising ammonia, propylene and oxygen.

DETAILED DESCRIPTION OF THE PREFERRED EMBODIMENT

Figure 1:
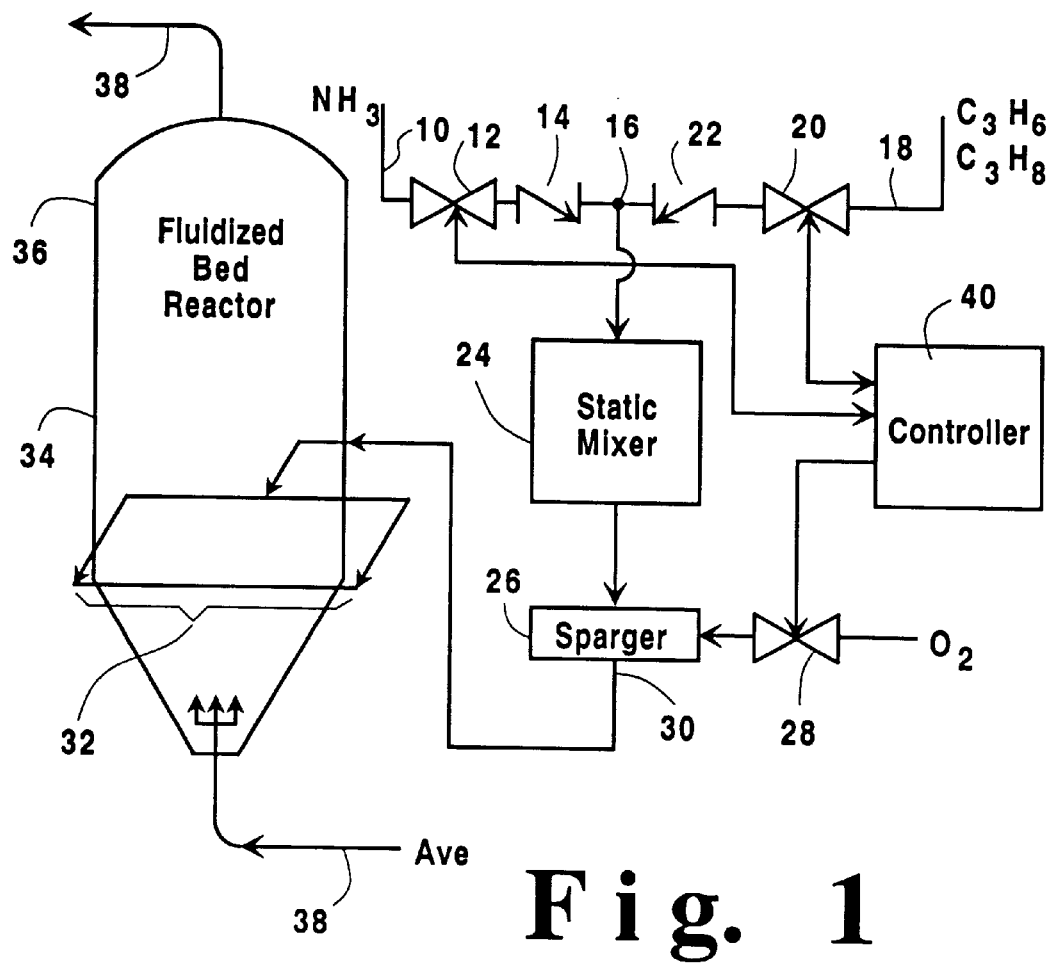
FIG. 1 is a block diagram of a system that embodies the invention hereof.

While the invention will hereafter be described in the context of an acrylonitrile ammoxidation process, those skilled in the art will realize that it is equally applicable to other processes which entrain an oxygen-containing gas with a reactant stream feed to a fluidized bed reactor. In FIG. 1, a system is shown for producing acrylonitrile using a fluidized bed ammoxidation process. A conduit 10 provides a flow of ammonia through a control valve 12, a check valve 14 to a T-junction 16. In similar fashion, a flow of propylene and propane are fed via conduit 18 through a control valve 20, check valve 22 to T-junction 16. There, the combined feed gases are fed to a static mixer 24 where they are combined into a mixed gaseous reactant stream that is, in turn, fed to a sparger 26. An oxygen source is connected via a control valve 28 to sparger 26.

Sparger 26 thereby enables oxygen to be entrained into the mixed reactant gas stream and to pass via conduit 30 to feedlines 32. Feedlines 32 are in direct contact with a fluidized bed 34 which comprises a particulate catalyst that facilitates a reaction occurring between the ammonia, propylene and oxygen constituents to produce an acrylonitrile product. That product is output from reactor 36 via conduit 38 where it is subjected to further processing. At the bottom of reactor 36 is an air feed 38 which provides additional oxygen for the reaction.

A controller 40 includes control connections to each of valves 12, 20 and 28 and serves to control reactant feeds therethrough in accordance with sensed process conditions. While a single controller 40 is shown in the Fig., those skilled in the art will realize that plural controllers can be used to control the respective valves and other control entities. The process inputs to controller 40 are not shown in the Fig.

Controller 40 (under operator control) assures that sufficient oxygen is injected by sparger 26 into the feed stream to assure, at the points of injection within fluidized bed reactor 36, that sufficient oxygen is present to prevent an oxygen deficiency at such points of injection. Controller further assures that the mixed concentration of reactants and oxygen is kept above an upper flammability limit (UFL) of the mixture. An acceptable safety margin of at least 25%, and preferably 50%, should be maintained.

The direct injection of oxygen with the reactants enables a concentration of oxygen at the region of feed injection which enables both a yield improvement and lifetime extension. Air flow into reactor 36, via conduit 38 also is adjusted to assure that the proper amount of oxygen is entrained within the reactor fluidized bed to enable optimum reaction conditions to be achieved. It is vital to the invention that plural oxygen supplies be provided to fluidized bed reactor 36, one supply assuring a proper oxygen concentration at the immediate regions of feed injection and the second oxygen supply assuring overall appropriate oxygen availability within the fluidized bed to enable proper reaction conditions to be achieved.

As indicated above, the feed flow of oxygen through sparger 26 is maintained at a level to assure that the upper flammability limit of the mixed reactant gas stream is exceeded. Table 1 below shows both the upper and lower flammability limits (UFL and LFL) for a propylene/ammonia feed stream in 100% oxygen.

TABLE 1

Calculated Flammability Limits in 100% oxygen

|  | LFL | UFL |
| --- | --- | --- |
| Propylene Feed[a] | 2.3 | 53.5 |
| Ammonia Feed[b] | 14.6 | 79.7 |
| Combined Feed[c] | 4.1 | 64.6 |

Figure 2:
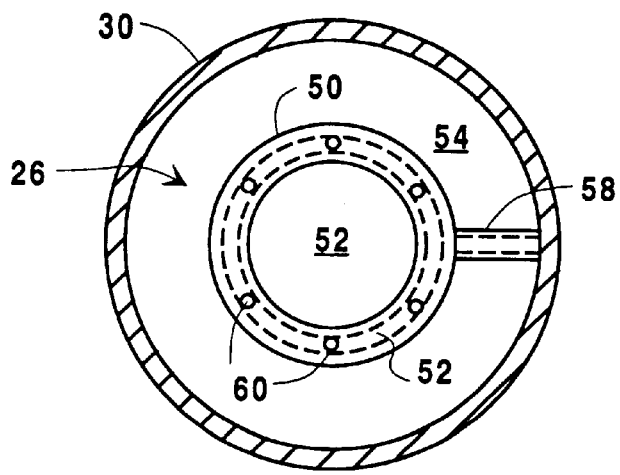
FIG. 2 is a sectional view of a feed pipe which includes a sparger for introducing oxygen into a gaseous feed stream.

[a]94% propylene, 6% propane, 150° F., 30 psig
[b]100% ammonia, 150° F., 30 psig
[b]52.4% ammonia, 44.7% propylene, 2.9% propane, 150° F., 30 psig Sparger 26 is shaped to allow its injectors to be arranged in pattern that achieves effective oxygen distribution throughout the reactant gas flow. The injectors are further positioned so as to prevent interaction of flammable mixtures which occur within the feed stream. In FIG. 2, sparger 26 is positioned within conduit 30 and is preferably shaped in the form of a single ring 50 that is positioned normal to the feed gas flow. To achieve good gas distribution, the inner and outer diameters of ring 50 are set so that there is substantially equal gas flow in regions 52 and 54, respectively. This arrangement assures that a low pressure area is not formed in the feed pipe within the ring of injectors (which would draw together the jets, cause a coalescence thereof and create a severe problem in the event of an ignition of one of the jet's). Thus, the effective cross-sectional areas of regions 52 and 54 are made approximately equal by appropriate sizing of ring 50.

Within ring 50 is a channel 56 which communicates with valve 28 (see FIG. 1) via inlet 58. A plurality of fixed jets 60 are positioned about ring 50 and are oriented so as to direct oxygen outflow from channel 56 in a downstream direction within conduit 30.

Figure 3:
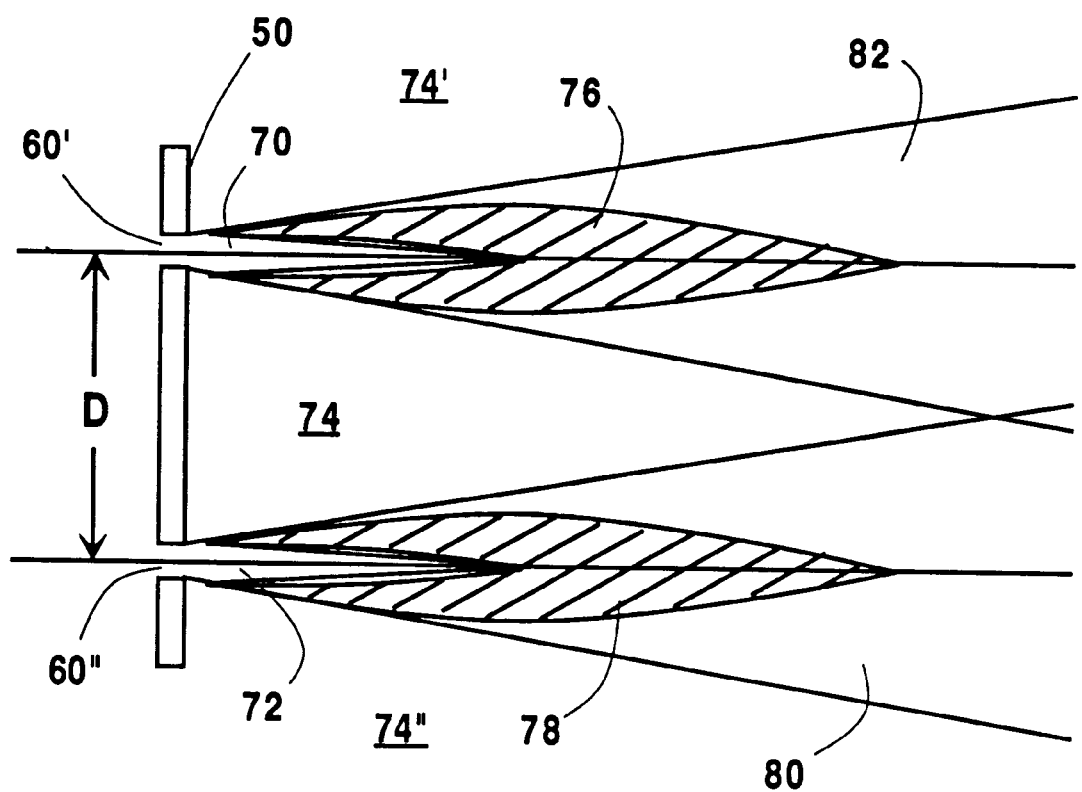
FIG. 3 is a schematic view of a pair of adjacent jets of the sparger of FIG. 2.

A sectional view of a pair of jets 60' and 60" is shown in FIG. 3. Oxygen flows out of jets 60' and 60" and creates substantially pure oxygen regions 70 and 72. The mixed reactant feed gas is present in regions 74, 74' and 74". Within regions 76 and 78 (cross-hatched), a mixture of oxygen and reactants occurs which is within the flammable ranges. Further downstream (regions 80 and 82), the gaseous mixture is non-flammable, even though oxygen bearing.

The spacing D between adjacent jets 60' and 60" is adjusted so that the flammable regions 76 and 78 do not interact. The limitation of jet-to-jet interaction reduces the probability of a once ignited jet causing ignition of another jet and of the jets coalescing to form a single jet with a large flame volume. The orifices of adjacent jets are thus placed so that neighboring regions of flammable gas mixture do not interact. Further, the mixed gas regions from adjacent jets intersect at a point beyond the farthest extent of the flammable regions. The risk of ignition is further reduced by lowering the total combined flammable volume contained within each oxygen jet. This is accomplished by minimizing the orifice diameter of each jet which, in turn, tends to maximize the number of orifices to accomplish a desired oxygen flow level.

The distance between a center of one orifice to the center of an adjacent orifice is given by:

$$D > d_0 \{258.7 - UFL)/(100 - UFL)\}$$

where: D=center–center distance between orifices; $d_0$=orifice diameter; UFL=upper flammability limit (in percent).

A risk of sustained jet deflagration is further reduced by insuring that the oxygen jet velocity is appreciably greater than both the velocity of the gaseous feed reactants and the flame velocity of a flammable oxygen reactant mixture. Such a jet velocity promotes flame blowoff, should flaming occur. To encourage blowoff, the initial oxygen jet velocity is preferably at least twice either the feed velocity of the reactant stream or flame velocity, which ever is greater. Further, the sparger is not to be constructed out of square shaped tube or to be supported with angle iron. Such structures include sharp angles which create eddies that can enhance flame stability.

Returning to FIG. 1, controller 40 operates valves 12, 20 and 28 to provide about one part ammonia, one part propylene and ten parts of air to fluidized bed reactor 36. The injection of oxygen, via valve 28 and sparger 26, enables a modest reduction in air flow via conduit 28. In addition to assuring that the combined reactant/oxygen flow in conduit 30 is in excess of the upper flammability level, it is preferred that the volumetric outflow from sparger 26 does not exceed a relative volumetric flow as follows: oxygen 30%; ammonia 35%; and propylene 35%. More preferably, the volumetric ratios are as follows: 10% oxygen; 45% ammonia; and 45% propylene.

If oxygen flow is suddenly increased or the reactant feed flow suddenly decreased, it is possible that the output from sparger 26 may move into a detonatable region. To control a sudden increase in oxygen flow, valve 28 is provided with a critical flow orifice which limits the possible oxygen flow. The orifice is sized so that even if valve 28 fails in the full-open state, the amount of oxygen required to produce a detonation under normal minimum feed flow rates cannot be supplied.

During emergency process shutdown, so long as the oxygen flow to sparger 26 is shut down simultaneously with the process reactants, the oxygen flow will be stopped simultaneously with the stoppage of reactant flow. Since oxygen valve 28 is significantly smaller than either of feed valves 12 and 20, the oxygen flow will stop before the flow of reactants—thereby preventing a feed concentration build-up to a detonatable level.

Controller 40 is operated to shut the oxygen flow to sparger 26 if the feed reactant pressures drop below a certain level. This is because a significant drop in feedflow can be brought about by feed blockage and a pressure-based shut-down response of valve 28 prevents a possible subsequent detonatable mixture from entering conduit 30.

Additionally, controller 40 is operated to shut the oxygen flow to sparger 26 if the temperature of the mixed oxygen reactant stream goes above a certain level. This is because a significant increase in gas mixture temperature can be brought about by a deflagration near the sparger and a temperature-based shut-down response of valve 28 will extinguish such a deflagration.

Valve 28 is also controlled by controller 40 to assure certain minimum oxygen flows to sparger 26. In operation, reactant feed must be prevented from backstreaming into sparger 26. This is prevented by: maintaining an oxygen flow through each sparger jet 60; maintaining a jet velocity that is great enough to prevent a convective or diffusive flow of the reactant feed into sparger 26; and placing the jets on the downstream side of sparger 26. The maintenance of oxygen flow through each sparger jet 60 is accomplished by insuring that the pressure drop across the jets 60 is significantly greater than the pressure drop within sparger 26. To prevent the reactant feed from diffusing into sparger 26, it is preferred that a minimum pressure drop across each jet 60 be at least 1 psi and preferably 10 psi.

Finally, during startup, a nitrogen purge is used to flush sparger 26 of reactants before oxygen flow begins. During shutdown, sparger 26 is flushed of oxygen with a nitrogen purge while maintaining a high enough pressure drop to prevent backstreaming. This is necessary because reactants will flow into sparger 26 after shutdown.

While sparger 26 has been shown in the shape of a ring, other shapes such as concentric rings, crossed straight sections and straight tubing are acceptable. However, each such structure must meet the requirements set forth above with respect to the most preferred embodiment, i.e., the circular sparger configuration shown in FIG. 2. Rather than placing the jets directly on the downstream edge of sparger 26, they can be placed off center, but still on the downstream side. This may be beneficial as it allows for a greater number of jets to be employed.

While the above description has focused on use of the invention in an acrylonitrile production process, other gas phase oxidations that use fluidized beds may also employ the invention (e.g., processes for the production of maleic anhydride, phthalic anhydride synthesis, etc.).

While not as preferred, inert gases may be added to either the oxygen or the reactant feed streams to lower the upper fire limit and thus increase the maximum concentration of oxygen allowed in the feed stream.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A system for providing a mixture of an oxygen-bearing gas and a gaseous reactant stream to a fluidized bed reactor to produce nitriles, comprising:

a source of a first oxygen-bearing gas coupled to said fluidized bed reactor;

a reactant gas stream comprising ammonia and propylene;

sparger means for entraining oxygen into said reactant gas stream;

feed means coupling said sparger means to said fluidized bed of said reactor, for introducing said reactant gas stream and entrained oxygen directly into contact with said fluidized bed; and control means for controlling feed of said oxygen to said sparger means so as to entrain sufficient oxygen into said reactant gas stream to assure that said fluidized bed experiences an oxygen sufficiency at a point of feed injection of said reactant gas stream and entrained second oxygen-bearing gas for production of said nitriles.

2. The system as recited in claim 1, wherein said fluidized bed comprises a catalyst for converting said ammonia, propylene and oxygen-into an acrylonitrile, said first oxygen-bearing gas is air, and wherein said control means controls oxygen feed to said sparger means so as to entrain sufficient oxygen into said ammonia and propylene gas stream to assure that said fluidized bed catalyst receives sufficient oxygen to prevent an oxygen deficiency at a point of feed injection of said gas stream.

3. The system as recited in claim 2, wherein said control means is coupled to plural sources of gaseous reactants which comprise said reactant gas stream and adjusts feeds of said gaseous reactants and oxygen to assure that said reactant gas stream and oxygen is maintained above an upper flammability limit.

4. The system as recited in claim 1, wherein said control means adjusts feeds of gaseous reactants to said reactant gas stream and said oxygen to assure that a combined said reactant gas stream and second oxygen-bearing gas is maintained above an upper flammability limit.

5. The system as recited in claim 4, wherein said sparger means comprises:

a pipe coupling said mixer means to said feed means; and a conduit positioned within said pipe, transverse to gas flow in said pipe, and connected to a source of said oxygen, said conduit provided with openings pointing downstream in said pipe for injecting said oxygen into said reactant gas stream.

6. The system as recited in claim 5, wherein said conduit is circular and provides a continuous interior flow path for said oxygen.

7. The system as recited in claim 5, wherein said conduit is a closed multi-sided polygon and provides a continuous interior flow path for said oxygen.

8. The system as recited in claim 6, wherein an outer circumference and an inner circumference of said circular conduit are sized so that approximately equal volumes of said mixed reactant gases flow between said outer circumference and an inner surface of said pipe and within said inner circumference.

9. The system as recited in claim 6, wherein said openings are positioned sufficiently far apart on said conduit to prevent flammable mixtures of said reactant gases and said oxygen from interacting downstream from adjacent openings.

10. The system as recited in claim 9, wherein said openings are of fixed size, said oxygen-bearing gas is oxygen, and flow of oxygen through said jet openings is pressure-controlled by said control means to assure that no reactant gases flow into said sparger means during operation of said system.

* * * * *